United States Patent

Alpegiani et al.

Patent Number: 5,089,489
Date of Patent: Feb. 18, 1992

[54] 6-SUBSTITUTED PENEM ESTERS AS ANTI-INFLAMMATORY AND ANTI-DEGENERATIVE AGENTS

[75] Inventors: Marco Alpegiani; Ettore Perrone, both of Milan; Piergiuseppe Orezzi, Genova; Paolo Carminati, Milan; Giuseppe Cassinelli, Pavia, all of Italy

[73] Assignee: Farmitalia Carlo Erba S.r.l., Milan, Italy

[21] Appl. No.: 504,836

[22] Filed: Apr. 5, 1990

Related U.S. Application Data

[62] Division of Ser. No. 206,375, Jun. 14, 1988, Pat. No. 4,954,493.

[30] Foreign Application Priority Data

Jun. 19, 1987 [GB] United Kingdom ............ 8714413

[51] Int. Cl.⁵ ............... C07D 499/00; A61K 31/425
[52] U.S. Cl. ................... 514/195; 514/192; 540/310
[58] Field of Search ............. 540/310; 514/192, 195

[56] References Cited

U.S. PATENT DOCUMENTS

| | | | |
|---|---|---|---|
| 4,482,565 | 11/1984 | Foglio et al. | 424/270 |
| 4,623,645 | 11/1986 | Doherty et al. | 540/215 |
| 4,711,886 | 12/1987 | Finke et al. | 540/310 |
| 4,797,396 | 1/1989 | Finke et al. | 514/210 |
| 4,847,247 | 7/1989 | Thompson et al. | 514/194 |
| 4,954,493 | 9/1990 | Alpegiani et al. | 514/195 |

FOREIGN PATENT DOCUMENTS

| | | |
|---|---|---|
| 85/4947 | 1/1985 | South Africa . |
| 2079744 | 1/1982 | United Kingdom . |
| 2104509 | 3/1983 | United Kingdom . |

OTHER PUBLICATIONS

*Heterocycles*, vol. 16, No. 11 (1981), pp. 1919-1921.
*Gazz. Chim. Ital.*, vol. 111 (9-10) (1981), pp. 371-377.
*Enzyme Kinetics*, Behavior and Analysis of Rapid Equilibrium and Steady-State Enzyme Systems, Irwin H. Segel, Wiley-Interscience Publication, John Wiley & Sons, New York, pp. 100-103, 110-111.

*Primary Examiner*—Nicholas S. Rizzo
*Attorney, Agent, or Firm*—Oblon, Spivak, McClelland, Maier & Neustadt

[57] ABSTRACT

6-substituted penem esters of formula (I):

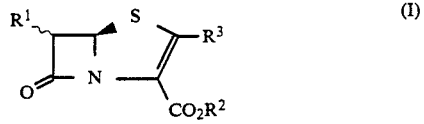

wherein $R_1$ is halogen or a $C_1$-$C_4$ alkyl, $C_1$-$C_4$ alkoxy, phenyl, phenoxy, benzyl or sulphonyloxy group; $R_2$ is a $C_1$-$C_4$ alkyl, benzyl diphenylmethyl

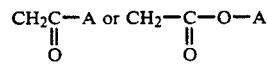

group where A is $C_1$-$C_4$ alkyl, benzyl, p-nitrobenzyl or p-methoxybenzyl; and $R_3$ is an organic radical, are elastase inhibitors and thereby useful antiinflammatory and antidegenerative agents.

5 Claims, No Drawings

6-SUBSTITUTED PENEM ESTERS AS ANTI-INFLAMMATORY AND ANTI-DEGENERATIVE AGENTS

This is a division of application Ser. No. 07/206,375, filed on June 14, 1988, now U.S. Pat. No. 4,954,493.

The present invention is concerned with protease inhibitors, especially human leukocyte elastase (HLE) inhibitors, useful in the prevention, control and treatment of inflammatory and degenerative diseases caused by proteolytic enzymes, in particular emphysema and rheumatoid arthritis.

The compounds with which the present invention is concerned are penem-3-carboxylic esters possessing an α- or β-oriented side chain at $C_6$. They may either be new, or be already known as intermediates for the corresponding penem-3-carboxylic acids (which may be known as antibacterial agents, but do not possess any protease-inhibiting activity). The present invention accordingly provides the use in the preparation of a medicament for use in treating inflammatory or degenerative conditions, especially such conditions caused by proteolytic enzymes, of compounds of formula (I):

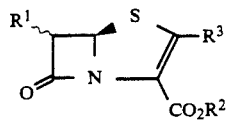

wherein
$R^1$ is
(1) chloro, bromo or fluoro;
(2) $C_1$–$C_4$ alkyl;
(3) $C_1$–$C_4$ alkoxy;
(4) phenyl, phenoxy or benzyl; or
(5) sulphonyloxy $RSO_2O$—, wherein R is either $C_1$–$C_4$ alkyl, aryl such as phenyl or naphthyl, arylalkyl such as benzyl, p-aminobenzyl or p-tolyl, or adamantyl-;

$R^2$ is
(1) $C_1$–$C_4$ alkyl;
(2) benzyl;
(3) diphenylmethyl;
(4) $CH_2$

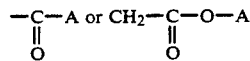

wherein A represents a group selected from methyl, ethyl, isopropyl, tert-butyl, benzyl, p-nitrobenzyl and p-methoxybenzyl; or
(5) —$(CH_2)_m$—COOB wherein B is a hydrogen atom or a negative charge and m is 1, 2 or 3; and $R^3$ is
(1)

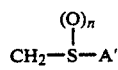

wherein A' represents:
(i) an organic radical selected from $C_1$–$C_4$ alkyl unsubstituted or substituted by fluoro; benzyl; and phenyl either unsubstituted or substituted by one or more group or atom chosen from nitro, amino, aminomethyl, azidomethyl, (N-pyridinio)methyl, hydroxy, hydroxymethyl, methyl and chloro; or
(ii) a saturated or unsaturated mono- or bicyclic ring which contains at least one heteroatom chosen from O, S and N and which is unsubstituted or substituted by an atom or group chosen from halogen such as chloro, $C_1$–$C_4$ alkyl such as methyl, oxo, phenyl, benzyl, amino, carboxy, $C_1$–$C_3$ alkoxycarbonyl, hydroxymethyl and hydroxy; and n is either 1 or 2;

(2) $CH_2Z$ wherein Z represents:
(i) a saturated or unsaturated mono- or bicyclic ring which contains at least one heteroatom chosen from O, S and N, which is linked to the $CH_2$ group through a carbon atom and which is unsubstituted or substituted by an atom or group chosen from halogen, $C_1$–$C_4$ alkyl, oxo, phenyl, benzyl, amino, carboxy, $C_1$–$C_3$ alkoxycarbonyl, hydroxymethyl and hydroxy; or
(ii) phenyl substituted by one or more atom or group chosen from chloro, methyl, nitro, amino, aminomethyl, 1-aminoethyl, N-pyridinio hydroxymethyl or hydroxy;

(3) substituted phenyl or ($C_1$–$C_4$ alkyl)phenyl such as α-methyl-phenyl;
(4) $C_3$–$C_7$ cycloalkyl or ($C_2$–$C_4$ acyloxy)($C_1$–$C_4$ alkyl) such as $CH_3COO(CH_2)_3$;
(5) 1-aminoethyl;
(6) a heterocyclic ring, 5- or 6-membered, saturated or unsaturated, containing at least one heteroatom chosen from O, S and N, linked to the penem ring through a carbon or nitrogen atom and optionally substituted by $C_1$–$C_4$ alkyl, halogen, phenyl, benzyl, amino, hydroxymethyl, carboxy, $C_1$–$C_3$ alkoxycarbonyl, oxo or hydroxy;
(7) —COA" wherein A" is $C_1$–$C_4$ alkyl, phenyl or benzyl;
(8)

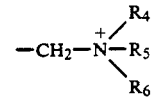

wherein
$R_4$ is $C_1$–$C_4$ alkyl and $R_5$ and $R_6$ taken together with the nitrogen atom to which they are attached represent a heterocyclic ring, 5- or 6-membered, saturated or unsaturated, containing at least one heteratom chosen from O, S and N, linked to the $CH_2$ group through a carbon or nitrogen atom and optionally substituted by $C_1$–$C_4$ alkyl, halogen, phenyl, benzyl, amino, hydroxymethyl, carboxy, $C_1$–$C_3$ alkoxycarbonyl, oxo or hydroxy; or
(9) —CH=CH—$R_7$ wherein $R_7$ is hydrogen, $C_1$–$C_4$ alkyl or,
(a) $CH_2$

(b) $CH_2SA'$,
(c) $CH_2OA'$,
(d) $CH_2A'$,
(e) OZ or SZ,
(f) carboxy,
(g) COOA, (h) COA'', (i) unsubstituted phenyl or (C$_1$-C$_4$ alkyl)phenyl, (j) a heterocyclic ring, 5- or 6-membered, saturated or unsaturated, containing at least one heteroatom chosen from O, S and N, linked to the =CH— group through a carbon or nitrogen atom and optionally substituted by C$_1$-C$_4$ alkyl, halogen, phenyl, benzyl, amino, hydroxymethyl, carboxy, C$_1$-C$_3$ alkoxycarbonyl, oxo or hydroxy, (k) fluoromethyl, difluoromethyl or trifluoromethyl, (l) amino (C$_1$-C$_4$ alkyl) such as 1-aminoethyl or aminomethyl, or (m) (N-phthalimido)-, (N-succinimido)- or (N-methylamino)-methyl, wherein A, A', A'' and Z are as defined above;

and pharmaceutically acceptable salts thereof.

The C$_1$-C$_4$ alkyl, C$_1$-C$_4$ alkoxy, phenyl, phenoxy, benzyl and aryl groups in the definitions (2), (3), (4) and (5) of R$^1$, (1) and (2) of R$^2$ and (3), (7), (8) and (9) of R$^3$ can be either unsubstituted or substituted by radicals chosen from methyl; methoxy; trifluoromethyl; fluoro; chloro; bromo; cyano; carboxy; sulfoamino; amino, carbamoyl, carbamoyloxy, guanidino, C$_1$ or C$_2$ aminoalkyl, C$_1$-C$_3$ carbamoylalkyl and C$_1$-C$_3$ carbamoyloxyalkyl wherein the amino, guanidino, carbamoyl and carbamoyloxy radicals can be optionally substituted at the nitrogen atom(s) by one or two methyl or ethyl groups; methylsulfonyl; azido; C$_2$-C$_5$ alkoxycarbonyl; benzyloxycarbonyl; acetyloxymethyl; trifluoroacetyloxymethyl; carboxymethyl; (C$_1$-C$_4$ alkoxy)carbonylmethyl; hydroxy; acylated hydroxy

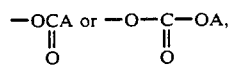

wherein A is as defined above; and formyloxy.

In particular, when R$_1$ is C$_1$-C$_4$ alkyl, preferred substituents for the alkyl group are fluoro, hydroxy, formyloxy, acetoxy, benzyloxy, methoxy, methoxycarbonyloxy, benzyloxycarbonyloxy and p-nitrobenzyloxycarbonyloxy; when R$^2$ is benzyl, preferred substituents for the benzyl group are nitro or methoxy in the ortho or para positions or o, p-dimethoxy; when R$^3$ is phenyl, preferred substituents for the phenyl group are methyl, trifluoromethyl, aminomethyl, acetyloxymethyl, trifluoroacetyloxymethyl, chloro and methoxy; when R$^3$ is

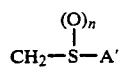

wherein A' represents a heterocyclic ring, such ring is preferably tetrazole, 1,3,4-thiadiazole, tetrazolo[1,5-δ]pyridazine, 1,3-thiazole.

The C$_1$-C$_4$ alkyl and C$_1$-C$_4$ alkoxy groups may be straight chain or branched chain groups. A C$_1$-C$_4$ alkyl group may be methyl, ethyl, n-propyl, iso-propyl, n-butyl, iso-butyl or tert.-butyl. The C$_1$-C$_4$ alkoxy group may be methoxy, ethoxy, n-propoxy, iso-propoxy, n-butoxy, iso-butoxy or tert.-butoxy. A preferred C$_2$-C$_4$ acyloxy group is acetoxy. Halogen is preferably chloro, bromo or fluoro. Preferred heterocyclic rings are tetrazole, triazole 1,3,4-thiadiazole, tetrazolo[1,5-b]pyridazine, 1,3-thiazole and pyridine, pyrazole, imidazole, furane, oxazole, indole.

In one embodiment, in formula (I) R$^1$ is selected from the group consisting of methyl, ethyl, propyl, phenyl, benzyl, hydroxymethyl, (1R)-hydroxyethyl, (1R)-fluoroethyl, benzyloxycarbonyloxymethyl, p-nitrobenzyloxycarbonyloxymethyl, 2-(acetoxy)-ethyl, 2-(p-nitrobenzyloxycarbonyloxy)ethyl, [(1R)-benzoyloxycarbonyloxyethyl], [(1R)-p-nitrobenzyloxycarbonyloxyethyl], [(1R)-phenylacetyloxyethyl] and methoxy; R$^2$ is selected from the group consisting of tert-butyl, benzyl, p-methoxybenzyl, p-nitrobenzyl, tert-butoxycarbonylmethyl and tert-butoxycarbonybenzyl; and R$_3$ is selected from the group consisting of methylsulfinylmethyl, methylsulfonylmethyl, phenylsulfinylmethyl, phenylsulfonylmethyl, phenyl, p-tolyl, p-(trifluoromethyl)phenyl and p-(trifluoroacetoxymethyl)phenyl.

In another embodiment, in formula (I) R$^1$ is CH$_3$, CH$_2$CH$_3$, Cl, F, OCH$_3$, OPh,

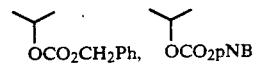

or —OSO$_2$R wherein Ph is phenyl, pNB is p-nitro-benzyl and R is methyl, phenyl, naphthyl, benzyl or p-aminobenzyl;

R$^2$ is (1')

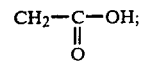

(3') benzyl optionally substituted by OCH$_3$, CO$_2$H, CO$_2$Et, CO$_2$Me, CO$_2$tert.butyl, CH$_2$CO$_2$H, CH$_2$CO$_2$Me or CH$_2$CO$_2$— tert.butyl; or (4') CH$_2$CO$_2$B' wherein B' is methyl, ethyl, tert.butyl or optionally substituted benzyl; and R$^3$ is (1') —CH$_2$—SO—Y or —CH$_2$—SO$_2$—Y wherein Y is methyl, CH$_2$F, benzyl, phenyl or p-nitro-phenyl;

(2') —CH$_2$Het wherein Het is

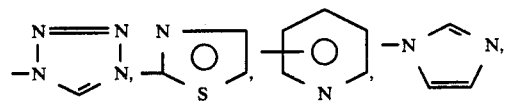

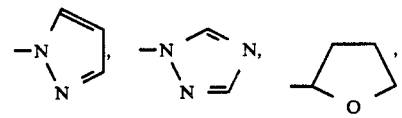

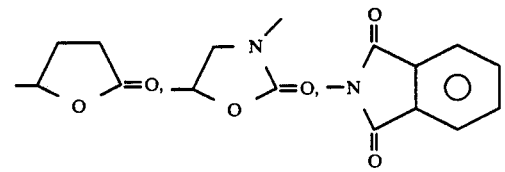

optionally substituted by $CH_3$, $CH_2OH$, phenyl, benzyl or halo;

(4') $(CH_2)_2OCOCH_3$;

(5') $-CH(CH_3)NH_2$ or $-CH_2CH(CH_3)-NH_2$ (7') $-COA''$ wherein $A''$ is a $C_1$-$C_4$ alkyl, phenyl, or benzyl;

(8')

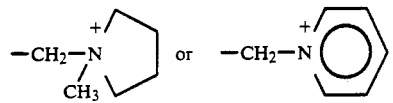

or (9') $-CH=CH-R'_7$ wherein $R'_7$ is $-CO_2H$; $-CO_2A$ wherein A is as defined above; $-CH_2OCOCH_3$; $-CH_2OCO$benzyl; $-CH_2OCONH_2$; $-CH_2OCONH$benzyl; $-CH_2OCONHCH_2CO_2H$ or an ester thereof; phenyl optionally substituted by $CH_3$, $CH_2OH$, $CH_2CO_2H$ or an ester thereof, $CO_2H$ or an ester thereof, aminomethyl, amino or

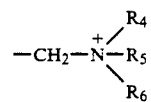

wherein $R_4$, $R_5$ and $R_6$ are as defined above.

The pharmaceutically acceptable salts of the compounds of formula (I) are the salts which may result from addition of an inorganic or organic acid or base when such compounds (I) have a salt-forming group, especially a carboxy, amino or quaternary ammonium group.

In the formulae in the specification, a dashed line ('''') indicates that a substituent is in the α-configuration, i.e. below the plane of the ring; a wedge-shaped line (◄) indicates that a substituent is in the β-configuration, i.e. above the plane of the ring; and a wavy line (∿) indicates that a substituent may be either in the α-configuration or in the β-configuration or both such as a racemic mixture.

Specific examples of the preferred compounds of the present invention are those cited herein below:

| no | $R^1$ | $R^1$ | $R^3$ |
|----|-------|-------|-------|
| 1 | Et | $CH_2Ph$ | $CH_2SOCH_3$ |
| 2 | " | " | $CH_2SOPh$ |
| 3 | " | " | $CH_2SO_2CH_3$ |
| 4 | " | " | $CH_2SO_2Ph$ |
| 5 | " | " | $CH_2$-pyridyl |
| 6 | " | " | $CH_2$-C(=N-N=N)-N(CH_3)$ (tetrazole derivative) |
| 7 | " | " | $CH_2$-C$_6$H$_4$-$NH_2$ |
| 8 | " | " | $CH_2$-C$_6$H$_4$-$CH_2OH$ |
| 9 | " | " | $CH_3$-C$_6$H$_3$-$Cl$ |
| 10 | " | " | C$_6$H$_4$-$CH_3$ |
| 11 | " | " | C$_6$H$_3$(CH_3)_2$ |

| no | R¹ | R¹ | R³ |
|---|---|---|---|
| | | | -continued |
| 12 | " | " | 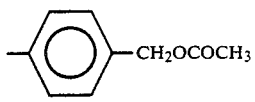 |
| 13 | " | " | 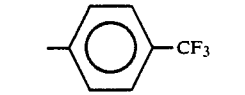 |
| 14 | " | " | 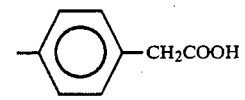 |
| 15 | " | " | 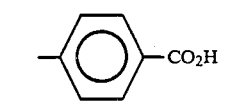 |
| 16 | Et | CH₂Ph | 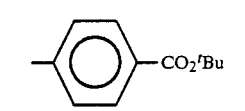 |
| 17 | " | " | 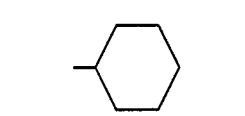 |
| 18 | " | " | 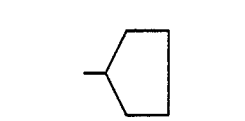 |
| 19 | " | " | 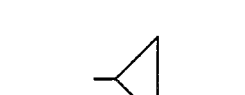 |
| 20 | " | " | CH₂CH₂CH₂OCOCH₃ |
| 21 | " | " | CH(NH₂)CH₃ |
| 22 | " | " | 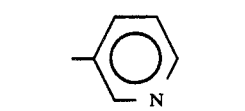 |
| 23 | " | " | 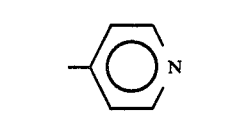 |
| 24 | " | " | 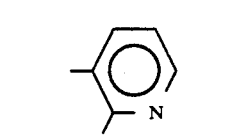 |
| 25 | " | " | 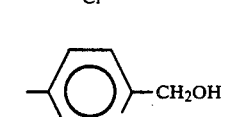 |

-continued

| no | R¹ | R¹ | R³ |
|---|---|---|---|
| 26 | " | " | 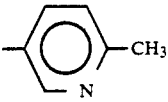 2-methyl-4-pyridyl |
| 27 | " | " | COCH₃ |
| 28 | " | " | COPh |
| 29 | " | " | 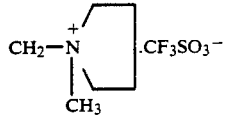 CH₂—N⁺(CH₃)₂ ring · CF₃SO₃⁻ |
| 30 | " | " | CH=CH₂ |
| 31 | " | " | CH=CH—CH₂SO₂CH₃ |
| 32 | " | " | CH=CH—CH₂SOPh |
| 33 | " | " | CH=CH—CH(CH₃)₂ |
| 34 | " | " | 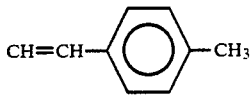 CH=CH—C₆H₄—CH₃ |
| 35 | " | " | CH=CH—CO₂H |
| 36 | " | " | CH=CH—CO₂ᵗBu |
| 37 | " | " | CH=CH—CH₂F |
| 38 | " | ᵗBu | CH₂SO₂CH₃ |
| 39 | " | " | CH₂SOPh |
| 40 | Cl | CH₂Ph | 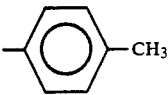 —C₆H₄—CH₃ |
| 41 | CH₃O | " |  CH₂—C₆H₄—CH₃ |
| 42 | CH₃OCH₂ | " | CH₂SOPh |
| 43 | pNBOCO₂CH₂ | CH₂Ph | CH₂SOPh |
| 44 | " | " | 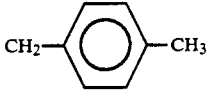 CH₂—C₆H₄—CH₃ |
| 45 | BzOCO₂CH₂ | " | CH₂SO₂CH₃ |
| 46 | " | " | 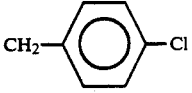 CH₂—C₆H₄—Cl |
| 47 | CH₃CH(OCO₂CH₂Ph) | " | CH₂SOPh |
| 48 | " | " | 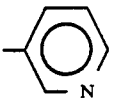 4-pyridyl |
| 49 | " | " | 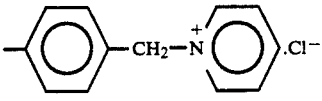 —C₆H₄—CH₂—N⁺(pyridyl) · Cl⁻ |
| 50 | CH₃CH(OCOCH₂Ph) | " | 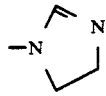 imidazolyl |

| no | R¹ | R¹ | R³ |
|---|---|---|---|
| 51 | " | " | CH₂SO₂CH₃ |
| 52 | " | " | 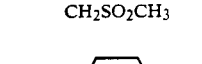 CH₂-⟨C₆H₄⟩-CH₃ |
| 53 | " | " | CH=CH—Ph |
| 54 | CH₃O | " | CH=CH—CH(CH₃)₂ |
| 55 | PhO | " | " |
| 56 | Ph | " | CH₂SO₂CH₃ |
| 57 | CH₃ | " | CH₂SOPh |
| 58 | Et | " | 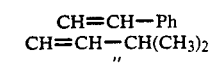 |

Bz represents benzyl; pNB represents p-nitro-benzyl

The compounds of formula (I) and pharmaceutically acceptable salts thereof can be prepared by a process comprising the thermal cyclization of a phosphorane-thioester of formula (II)

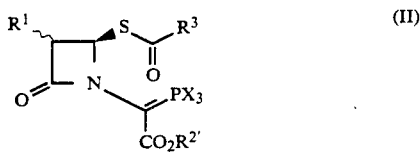

wherein $R^1$ and $R^3$ are as defined above, X is phenyl, methoxy or ethoxy and $R^{2'}$ is either $R^2$ as defined above or a carboxy protecting group, to obtain a penem of formula (I'):

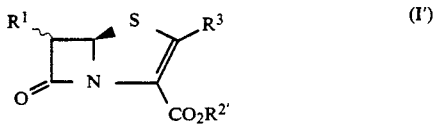

wherein $R^1$, $R^{2'}$ and $R^3$ are as defined above; removing the carboxy protecting group when present and replacing the said group by a $R^2$ group by esterification where $R^2$ is as defined above; and, if desired, converting a penem of formula (I) thus obtained into a pharmaceutically acceptable salt thereof.

The thermal cyclization of phosphorane-thioesters of formula (II) is carried out by heating in an inert organic solvent, e.g. chloroform, benzene, toluene, xylene or dioxane, at temperatures ranging from 15° C. to refluxing conditions.

When $R^{2'}$ is a carboxy-protecting group, it is preferably allyl, p-nitrobenzyl, p-methoxybenzyl or trichloroethyl. The removal of such protecting-groups from a compound of formula (I') is carried out by conventional methodologies, such as palladium-mediated transallilation when $R^{2'}$ is allyl (for the experimental conditions see P. D. Jeffrey and S. W. McCombie, *J. Org. Chem.* 1982, 47, 587; R. Deziel, Tetrahedron lett. 1987, 28, 4371); hydrogenolysis, especially over palladium on charcoal, when $R^{2'}$ is p-nitrobenzyl; exposure to Lewis acids, especially AlCl₃, in the presence of anisole and at low temperatures (from −75° C. to −40° C.) when $R^{2'}$ is p-methoxybenzyl; and dissolving metal conditions, especially with powdered Fe or Zn in an organic solvent, e.g. tetrahydrofuran or dichloromethane, optionally in the presence of a buffered water solution, when $R^{2'}$ is trichloroethyl or p-nitrobenzyl.

The compounds obtained by the above-detailed removals of carboxy-protecting groups can be esterified to the compounds of formula (I) by reaction with an alcohol of formula $R^2$ OH or with an alkyl or benzyl halide of formula $R^2X$, whereon $R^2$ is as defined above and X is chloro, bromo or iodo, or by reaction with diazoalkanes such as diazomethane, phenyl diazomethane and diphenyl diazomethane. Such esterification methodologies are well known per se (see for example, the Chemistry of Acid Derivatives, Saul Petai Ed., J. Wiley, NY, 1979, p 441) and is usually carried out under the same conditions adopted for the conversion of a penem or cephem carboxylic acid into an ester thereof (see, for example, Cephalosporins and Penicillins, E. Flynn Ed., Academic Press, NY, 1972, p 172).

The intermediates of formula (II) are known compounds or can be prepared from known compounds according to known methodologies (see, for example, I. Ernest et al., *J. Am. Chem. Soc.* 1978, 100, 8214 when X is phenyl and E. Perrone et al., *Tetrahedron Lett.* 1984, 25, 2399 when X is methoxy or ethoxy).

The potentialities of protease inhibitor therapy in the treatment of conditions resulting from the destruction of connective tissues have recently received particular attention.

Much effort has been devoted to the search for inhibitors of human leukocyte elastase (HLE), which is the primary destructive agent in pulmonary emphysema and is probably involved in rheumatoid arthritis (J. C. Power, Am. Rev. Resp. Diseases 127, S54–S58, 1983; C. H. Hassal et al., FEBS Letters, 183, n. 2, 201, 1985; G. Weinbaum and V. V. Damiano, TIPS, 8, 6, 1987; M. Velvart, Rheymatol. Int., 1, 121, 1981). Low molecular weight inhibitors appear to have a number of advantages over natural high molecular weight protease inhibitors from either plant or animal sources: 1) they can be obtained in quantities; 2) they can be rationally designed and optimized; 3) they are not antigenic; 4) they may be used orally or in aerosols. Many low molecular weight elastase inhibitors discovered so far contain reactive functional groups (chloromethyl ketones, isocyanates, etc.); they may react with functional groups of proteins, and therefore they may be quite toxic. In this respect β-lactam compounds are of potential interest because, though reactive towards serine proteases, they are, as it is known, non-toxic at very high concentrations.

To date, penem acids have been exclusively considered as antibacterial agents; penem esters, including some of the ones encompassed by the formula (I), have been considered as intermediates or pro-drugs for the corresponding antibacterial penem acids. Although some cephalosporin sulphones of formula (III):

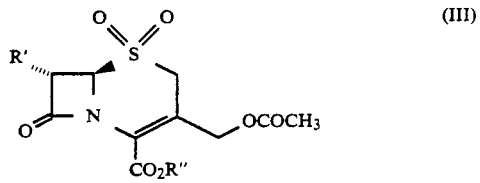

possess good HLE-inhibiting activity (J. B. Doherty et al., Nature, 1986, 322, 192), they require a sulphone group and a leaving group at $C_3$, especially an acetoxymethyl group.

Now, we have unexpectedly found that potent HLE-inhibitors can be found within the class of penems, in particular within the class of formula (I), which are not characterised by a sulphone group or by an acetoxymethyl group at $C_3$. Accordingly, owing to their high elastase-inhibiting activity and their quite negligible toxicity, the compounds of formula (I) and their pharmaceutically acceptable salts can be used to make medicaments useful to prevent or arrest the progression of diseases caused by proteolytic degradation of lungs and connective tissues, reduce inflammation and fever, and relieve pain. Such diseases are emphysema, acute respiratory distress syndrome, bronchial inflammation, rheumathoid arthritis, osteoarthritis, infectious arthritis, rheumatic fever, spondylitis, gout, lupus, psoriasis, and the like.

The compounds can be formulated as pharmaceutical compositions for administering the active penem esters of formula (I) and pharmaceutically acceptable salts thereof to humans or other mammalian species. The pharmaceutical or veterinary compositions containing these compounds may be prepared in a conventional way by employing conventional non-toxic pharmaceutically carriers or diluents, in a variety of dosage forms and ways of administration. In particular, the compounds can be administered:

(a) orally, for example, as tablets, troches, lozenges, aqueous or oily suspensions, dispersible powders or granules, emulsions, hard or soft capsules, or syrups of elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide a pharmaceutically elegant and palatable preparation.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate, granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropymethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products or ethylene oxide with partial esters derived from fatty acids and hexitol anhydrides, for example polyoxyethylene sorbitan monooleate.

The said aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth bove, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerl, sorbitol or sucrose. Such formulations may also contain a demulcent, a preservative and flavoring and coloring agents.

(b) parenterally, either subcutaneously, or intravenously, or intramuscularly, or intrasternally, or by infusion techniques, in the form of sterile injectable aqueous or oleagenous suspensions. The pharmaceutical compositions may be in the form of a sterile injectable aqueous or olagenous suspension.

This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

(c) by inhalation, in the form of aerosols or solutions for nebulizers;

(d) rectally, in the form of suppositories prepared by mixing the drug with a suitable non-irritating excipient which is solid at ordinary temperatures but liquid at the rectal temperature and will therefore melt in the rectum to release the drug. Such materials are cocoa butter and polyethylene glycols;

(e) topically, in the form of creams, ointments, jellies, solutions or suspensions.

Inflammatory and degenerative diseases can be controlled by administering a therapeutically effective amount of one or more of the compounds of formula (I) or pharmaceutically acceptable salts thereof to humans or other mammals in need of such treatment. Daily doses are in the range of about 0.5 to about 100 mg per kg of body weight, according to the activity of the specific compound, the age, weight and conditions of the subject to be treated, the type and severity of the disease, and the frequency and roue of administration. Preferably, daily dosage levels for humans are in the range of 50 mg to 2 g.

The amount of active ingredient that may be combined with the carrier materials to produce a single dosage form will vary depending upon the host treated and the particular mode of administration. For example, a formulation intended for oral administration of humans may contain from 5 mg to 5 g of active agent compounded with an appropriate and convenient amount of carrier material which may vary from about 5 to 95 percent of the total composition. Dosage unit forms will generally contain between from about 25 mg to about 500 mg of active ingredient.

The following Examples illustrate the invention.

EXAMPLE 1

Benzyl (5R,6S)-6-ethyl-2[(E)-2-(4-methylphenyl)ethenyl]-penem-3-carboxylate (Compound 34)

A solution of benzyl [(3S,4R)-4-argentiothio-3-ethyl-2-oxoazetidin-1-yl]triphenylphosphoranylideneacetate (0.65 g) in dichloromethane (80 ml) was stirred at room temperature for 20 min. in the presence of 3-(4-methylphenyl)ethenoyl chloride (0.23 g). The reaction mixture was filtered, washed with aq. NaHCO$_3$, dried over Na$_2$SO$_4$, filtered and evaporated. Silica gel chromatography afforded benzyl {(3S)-ethyl-(4R)-[3-(4-methylphenyl)ethenoylthio]-2-oxoazetidin-1-yl}triphenyl-phosphoranylideneacetate as a foam. This material was refluxed for 5 h. in toluene (80 ml). Chromatography afforded the title product as a yellowish powder; 250 mg.

IR(KBr) $\nu$ max 1778, 1685 cm$^{-1}$, NMR (90 MHz, CDCl$_3$) $\delta$ 1.05 (3H, t, J=7.4 Hz), 1.85 (2H, q, J=7.4 Hz), 2.32 (3H,s), 3.67 (1H, dt, J=1.7 and 7.4 Hz), 5.30 (3H, s+d, J=1.7 Hz), 6.74 and 7.92 (each 1H, d, J=16 Hz), 7.02–7.50 (9H, m) ppm; UV (CHCl$_3$) $\lambda_{max}$ 351 ($\epsilon$=(1800) and 378 ($\epsilon$=12840); MS (FD) 405 m/z (M$^+$).

EXAMPLE 2:

Benzyl (5R, 6S)-6-ethyl-2-(3-pyridyl)penem-3-carboxylate (Compound 22)

By a procedure similar to that detailed in Example 1, but substituting (3-pyridyl) carbonyl chloride for 3-(4-methylphenyl)ethenoyl chloride, the title product (260 mg) was obtained as a yellowish powder.

IR (KBr) $\nu$ max 1775, 1700 cm$^{-1}$, NMR (90 MHz, CDCl$_3$) $\delta$ 1.08 (3H, t, J=7.5 Hz), 1.92 (2H, dg, J=7.5 and 7 Hz), 3.80 (1H, dt; J=1.7 and 7 Hz), 5.10 (2H, s), 5.50 (1H, l, J=1.7 Hz) 7.1–7.4 (6H, m), 7.65–7.80 (1H, m), 8.57 (1H, dd, J=2 and 5 Hz), 8.66 (1H, d, J=2 Hz) ppm; UV (CHCl$_3$) $\lambda$ max 337 nm ($\epsilon$=6,550).

EXAMPLE 3

Benzyl (5R, 6S)-2-(benzo[b]thiophen-2-yl)-6-ethyl-penem-3-carboxylate (Compound 58)

By following a procedure similar to that detailed in Example 1, but substituting (2-benzo[b]thiophenyl)carbonyl chloride for 3-(4-methylphenyl)ethenoyl chloride, the title product (60 mg) was obtained as a yellowish powder.

IR (KBr) $\lambda$ max 1765, 1700 cm$^{-1}$; NMR (90 MHz, CDCl$_3$) $\delta$ 1.08 (3H, t, J=7.3 Hz), 1.85 (2H, 9, J=7.3 Hz), 3.75 (1H, dt, J=1.7 and 7.3 Hz), 5.27 (2H, s), 5.39 (1H, d, J=1.7 Hz), 7.2–7.9 (10H, m) ppm; UV (CHCl$_3$) $\lambda$ max 359 mm ($\epsilon$=10,241); MS (FD) 421 m/z (M$^+$).

We claim:

1. A method of treating or managing elastase-mediated diseases comprising the administration to mammalian species in need of such treatment an effective amount of a 6-substituted penem ester of formula (I):

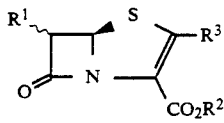

wherein
R¹ is
(1) chloro, bromo or fluoro;
(2) $C_1$-$C_4$ alkyl;
(3) $C_1$-$C_4$ alkoxy;
(4) phenyl, phenoxy or benzyl; or
(5) sulfonyloxy RSO₂O—, wherein R is either $C_1$-$C_4$ alkyl, aryl, arylalkyl, p-aminobenzyl, or adamantyl;
R² is
(1) $C_1$-$C_4$ alkyl;
(2) benzyl;
(3) diphenylmethyl;
(4) CH₂

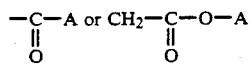

wherein A represents a group selected from methyl, ethyl, isopropyl, tert-butyl, benzyl, p-nitrobenzyl and p-methoxybenzyl; or
(5) —(CH₂)$_m$—COOB wherein B is a hydrogen atom or a negative charge and m is 1, 2 or 3; and
R³ is a heterocyclic ring, 5- or 6- membered, saturated or unsaturated, containing at least one heteroatom chosen from O, S and N, tetrazolo (1,5-b) pyridazine or thianaphthene linked to the penem ring through a carbon or nitrogen atom and optionally substituted by $C_1$-$C_4$ alkyl, halogen, phenyl, benzyl, amino, hydroxymethyl, carboxy, $C_1$-$C_3$ 3 alkoxycarbonyl, oxo or hydroxy; and
pharmaceutically acceptable salts thereof; the $C_1$-$C_4$ alkoxy, phenyl, phenoxy, and benzyl groups in the definitions (2), (3), (4) and (5) of R¹, and (1) and (2) of R² being either unsubstituted or substituted by radicals chosen from methyl, methoxy, trifluoromethyl, fluoro, chloro, bromo, cyano, carboxy, sulfoamino, amino, carbamoyl, carbamoyloxy, guanidino, $C_1$ or $C_2$ aminoalkyl, $C_1$-$C_3$ carbamoylalkyl and $C_1$-$C_3$ carbamoyloxyalkyl wherein the amino,. guanidino, carbamoyl and carbamoyloxy radicals can be optionally substituted at the nitrogen atom(s) by one or two methyl or ethyl groups; methysulfonyl, azido, $C_2$-$C_5$ alkoxycarbonyl, benzyloxycarbonyl, acetyloxymethyl, trifluoroacetyloxymethyl, carboxylmethyl, ($C_1$-$C_4$ alkoxy) carbonylmethyl, hydroxy, acylated hydroxy

wherein A is as defined above; and formyloxy.

2. A method according to claim 1, wherein
R¹ is:
(1) chloro, bromo or fluoro;
(2) $C_1$-$C_4$ alkyl;
(3) $C_1$-$C_4$ alkoxy;
(4) phenyl, phenoxy or benzyl; or
(5) sulfonyloxy RSO₂O—, wherein R is either $C_1$-$C_4$ alkyl, phenyl, naphthyl, benzyl, p-aminobenzyl, p-tolyl or adamantyl; and
R³ is: a heterocyclic group selected from thianaphthene, tetrazole, triazole, 1,3,4-thiadiazole, tetrazolo(1,5-b)pyridazine, 1,3-thiazole, pyridine, pyrazole, imidazole, furane, oxazole, and indole, unsubstituted or substituted by an atom or group chosen from halogen, $C_1$-$C_4$ alkyl, oxo, phenyl, benzyl, amino, carboxy, $C_1$-$C_3$ alkoxycarbonyl, hydroxymethyl and hydroxy.

3. A method according to claim 1, wherein in formula (I) R¹ is selected from the group consisting of chloro, methyl, ethyl, methoxy, methoxymethyl, phenyl, phenoxy, benzyloxycarbonyloxymethyl, p-nitrobenzyloxycarbonyloxymethyl, 1-benzylcarbonyloxyethyl; R² is selected from the group consisting of tert-butyl and benzyl; and R³ is selected from the group consisting of pyridin-3-yl, pyridin-4-yl, 2-chloro-pyridin-3-yl, 2-hydroxymethyl-pyridin-5yl, picolin-5-yl, 4,5-dihydroimidazol-1-yl, and thianaphthyl.

4. A method according to claim 1, wherein the 6-substituted penem ester is: benzyl (5R, 6S-6-ethyl-2-(3-pyridyl)penem-3-carboxylate.

5. A method according to claim 1, wherein the s6-substituted penem ester is: benzyl (5R, 6S)-2-(benzo(b)thiophen-2-yl)-6-ethyl-penem-3-carboxylate.

* * * * *